US00PP30322P3

(12) United States Plant Patent
Holtmaat

(10) Patent No.: US PP30,322 P3
(45) Date of Patent: Mar. 26, 2019

(54) ***ECHINACEA* PLANT NAMED 'SWEET342'**

(50) Latin Name: *Echinacea purpurea*
Varietal Denomination: Sweet342

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 15/731,581

(22) Filed: Jul. 3, 2017

(65) Prior Publication Data

US 2019/0008085 P1 Jan. 3, 2019

(51) Int. Cl.
*A01H 5/02* (2018.01)

(52) U.S. Cl.
USPC ..... Plt./428

(58) Field of Classification Search
USPC ..... Plt./428

CPC . A01H 5/025; A01H 5/02; A01H 5/00; A01H 6/14; A01H 6/1448
See application file for complete search history.

(56) References Cited

U.S. PATENT DOCUMENTS

PP24,631 P2 * 7/2014 Blom ..... A01H 5/00 Plt./428

OTHER PUBLICATIONS

Plants Nouveau 2016 Catalog Supplement (2017) retrieved on Jun. 4, 2018, retrieved from the Internet at https://issuu.com/angelatreadwell-palmer/docs/magazine0616, pp. 1-2 introductory and p. 7 (Year: 2017).*

* cited by examiner

*Primary Examiner* — June Hwu
(74) *Attorney, Agent, or Firm* — C. A. Whealy

(57) ABSTRACT

A new and distinct cultivar of *Echinacea* plant named 'Sweet342', characterized by its broadly upright plant habit; moderately vigorous growth habit; freely branching habit; strong flowering stems; numerous large single-type inflorescences with red purple-colored ray florets and red-colored receptacle spines with black-colored apices; and good garden performance.

2 Drawing Sheets

Botanical designation: *Echinacea purpurea.*
Cultivar denomination: 'SWEET342'.

BACKGROUND OF THE INVENTION

The present invention relates to a new and distinct cultivar of *Echinacea* plant, botanically known as *Echinacea purpurea*, and hereinafter referred to by the name 'Sweet342'.

The new *Echinacea* plant is a product of a planned breeding program conducted by the Inventor in Zuidwolde, The Netherlands. The objective of the breeding program is to develop new freely branching and relatively compact *Echinacea* plants with unique and attractive ray floret coloration.

The new *Echinacea* plant originated from an open-pollination in July, 2014 in Zuidwolde, The Netherlands of an unnamed seedling selection of *Echinacea purpurea*, not patented, as the female, or seed, parent with an unknown selection of *Echinacea purpurea* as the male, or pollen, parent. The new *Echinacea* plant was discovered and selected by the Inventor as a single flowering plant from within the progeny of the stated open-pollination grown in a controlled greenhouse environment in Zuidwolde, The Netherlands in July, 2015.

Asexual reproduction of the new *Echinacea* plant by in vitro meristem culture in a controlled environment in Zuidwolde, The Netherlands since June, 2016 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Sweet342'. These characteristics in combination distinguish 'Sweet342' as a new and distinct *Echinacea* plant:

1. Broadly upright plant habit.
2. Moderately vigorous growth habit.
3. Freely branching habit.
4. Strong flowering stems.
5. Numerous large single-type inflorescences with red purple- colored ray florets and red-colored receptacle spines with black-colored apices.
6. Good garden performance.

Plants of the new *Echinacea* can be compared to plants of the female parent selection. Plants of the new *Echinacea* differ primarily from plants of the female parent selection in the following characteristics:

1. Plants of the new *Echinacea* are more uniform than plants of the female parent selection.
2. Plants of the new *Echinacea* are more freely flowering than plants of the female parent selection.

Plants of the new *Echinacea* can be compared to plants of *Echinacea hybrida* 'Cleopatra', disclosed in U.S. Plant Pat. No. 24,631. In side-by-side comparisons, plants of the new *Echinacea* differ primarily from plants of 'Cleopatra' in the following characteristics:

1. Plants of the new *Echinacea* are taller than plants of 'Cleopatra'.
2. Plants of the new *Echinacea* are more freely flowering than plants of 'Cleopatra'.
3. Plants of the new *Echinacea* have larger inflorescences than plants of 'Cleopatra'.
4. Plants of the new *Echinacea* have red purple-colored ray florets whereas plants of 'Cleopatra' have yellow-colored ray florets.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photographs on the first sheet are side perspective views of a typical flowering plant (upper photograph) grown in a ground bed in an outdoor nursery and placed in a container for the photograph and a group of typical flowering plants (lower photograph) of 'Sweet342' grown in a ground bed in an outdoor nursery.

The photographs on the second sheet are close-up views of a typical inflorescence (upper photograph) and the upper surface of typical leaves (lower photograph) of 'Sweet342'.

DETAILED BOTANICAL DESCRIPTION

The aforementioned photographs and following observations and measurements describe plants grown during the summer in ground beds in an outdoor nursery in Zuidwolde, The Netherlands and under cultural practices typically used in commercial *Echinacea* production. During the production of the plants, day temperatures ranged from 18° C. to 30° C. and night temperatures ranged from 6° C. to 18° C. Plants were six months old when the photographs and description were taken. In the following description, color references are made to The Royal Horticultural Society Colour Chart, 2015 Edition, except where general terms of ordinary dictionary significance are used.

Botanical classification: *Echinacea purpurea* 'Sweet342'.

Parentage:

*Female parent*.—Unnamed seedling selection of *Echinacea purpurea*, not patented.

*Male parent*.—Unknown selection of *Echinacea purpurea*, not patented.

Propagation:

*Type*.—By in vitro meristem culture.

*Time to initiate roots, summer*.—About one week at temperatures about 25° C.

*Time to produce a rooted young plant, summer*.—About five weeks at temperatures about 21° C.

*Root description*.—Fine, fibrous; typically pale cream in color, actual color of the roots is dependent on substrate composition, water quality, fertilizer type and formulation, substrate temperature and physiological age of roots.

*Rooting habit*.—Freely branching; dense.

Plant description:

*Plant form and growth habit*.—Herbaceous perennial; broadly upright plant habit, narrow inverted triangle; freely branching habit with about ten lateral branches developing per primary branch; moderately vigorous growth habit; moderate growth rate.

*Plant height, soil level to top of foliar plane*.—About 49.7 cm.

*Plant height, soil level to top of floral plane*.—About 61.5 cm.

*Plant diameter or spread*.—About 51.5 cm.

*Lateral branches*.—Length: About 31 cm. Diameter: About 8 mm. Internode length: About 4.7 cm. Aspect: About 25° from vertical. Strength: Moderately strong. Texture and luster: Densely pubescent; moderately glossy. Color: Close to 144A.

Leaf description:

*Basal leaves*.—Arrangement: Alternate, simple. Length: About 18.3 cm. Width: About 9.6 cm. Shape: Ovate. Apex: Acute. Base: Attenuate. Margin: Entire, occasionally shallowly to coarsely dentate. Texture and luster, upper and lower surfaces: Moderately pubescent, strigose, rough, slightly rugose; slightly glossy. Venation pattern: Pinnate. Color: Developing leaves, upper and lower surfaces: Close to 143A. Fully expanded leaves, upper surface: Slightly darker than between NN137A and 147A; venation, close to 144A. Fully expanded leaves, lower surface: Close to 147B; venation, close to 144B. Petioles, basal leaves: Length: About 9.6 cm. Width: About 3 mm. Height: About 3 mm. Strength: Strong, flexible. Texture and luster, upper and lower surfaces: Sparsely pubescent; glossy. Color, upper surface: Close to 144B strongly tinged with close to between N186C and N186D. Color, lower surface: Close to 144A slightly tinged with close to N186D.

*Cauline leaves*.—Arrangement: Alternate, simple. Length: About 8.2 cm. Width: About 3.2 cm. Shape: Ovate. Apex: Acute. Base: Attenuate. Margin: Entire, occasionally shallowly to coarsely dentate. Texture and luster, upper and lower surfaces: Moderately pubescent, strigose; slightly glossy. Venation pattern: Pinnate. Color: Developing leaves, upper and lower surfaces: Close to 143A. Fully expanded leaves, upper surface: Slightly darker than between NN137A and 147A; venation, close to 144A. Fully expanded leaves, lower surface: Close to 147B; venation, close to 144B. Petioles, cauline leaves: Length: About 1.6 cm. Width: About 2 mm. Height: About 2 mm. Strength: Strong, flexible. Texture and luster, upper and lower surfaces: Sparsely pubescent; glossy. Color, upper surface: Close to 144B strongly tinged with close to between N186C and N186D. Color, lower surface: Close to 144B slightly tinged with close to N186D.

Inflorescence description:

*Appearance*.—Large single-type inflorescences with ray and disc florets arranged on a capitulum; inflorescences positioned upright above the foliar plane on strong peduncles.

*Flowering habit*.—Freely flowering habit with about 30 inflorescences developing per plant during the flowering season.

*Fragrance*.—Moderately fragrant, slightly acidic and pleasant.

*Time to flower*.—Plants begin flowering about 100 days after planting; in the garden, plants flower continuously during the summer in The Netherlands.

*Inflorescence longevity*.—Inflorescences maintain good substance for about two weeks on the plant; inflorescences not persistent.

*Inflorescence buds*.—Height: About 3.5 cm. Diameter: About 4.8 cm. Shape: Flattened globular. Texture and luster: Smooth, glabrous; matte. Color: Involucral bracts, close to N186C; developing ray florets, close to 46B.

*Inflorescence size*.—Diameter: About 11.4 cm. Depth (height): About 4.2 cm. Disc diameter: About 4 cm.

*Receptacles*.—Height: About 1.2 cm. Diameter: About 9 mm. Color: Close to 155C.

*Ray florets*.—Quantity and arrangement: About 26 arranged in a single whorl. Length: About 5.3 cm. Width: About 1.3 cm. Shape: Oblanceolate; straight, not twisting. Apex: Emarginate. Base: Cuneate. Margin: Entire. Texture and luster, upper surface: Smooth, glabrous, moderately velvety; matte. Texture and luster, lower surface: Smooth, glabrous, slightly velvety; slightly glossy. Aspect: Outward, close to horizontal. Color: When opening, upper surface: Close to 46A. When opening, lower surface: Close to 60C. Fully opened, upper surface: Close to 53A; venation, close to 53A; color becoming closer to 59B with development. Fully opened, lower surface: Close to 60C; venation, close to 60C; color does not change with development.

*Disc florets*.—Quantity and arrangement: About 300 per inflorescence, arranged spirally at the center of the receptacle. Length: About 1.1 cm. Diameter: About 3.5 mm. Shape: Tubular; proximally, 17.5% free, not fused. Apex: Acute. Base: Fused. Margin: Entire. Aspect: Mostly upright. Texture and luster, inner and outer surfaces: Smooth, glabrous; glossy. Color, when opening, inner and outer surfaces: Apex: Close to 147C tinged with close to 183A. Mid-section: Close to 147C. Base: Close to 187C. Color, fully opened, inner and outer surfaces: Apex: Close to 147C tinged with close to 183A. Mid-section: Close to 147C. Base: Close to 187C.

*Receptacle spines*.—Quantity: One per disc floret. Length: About 1.5 cm. Diameter: About 1.5 mm. Shape: Acicular. Apex: Narrowly acute. Base: Cuneate. Texture and luster: Smooth, glabrous; glossy. Color: Apex, lower surface: Close to 203A. Mid-section: Distally, close to 42B; proximally, close to 23A. Base: Close to 144B.

*Involucral bracts*.—Quantity per inflorescence: About 80 arranged in about four whorls. Length: About 1.2 cm. Width: About 3.5 mm. Shape: Narrowly ovate. Apex: Acute. Base: Cuneate. Margin: Entire; moderately pubescent. Texture and luster, upper and lower surfaces: Smooth, glabrous; slightly glossy. Color, upper surface: Close to 137B. Color, lower surface: Close to 143B.

*Peduncles*.—Length, terminal peduncle: About 13.1 cm. Diameter, terminal peduncle: About 5 mm. Strength: Strong. Aspect, terminal peduncle: Upright. Texture and luster: Moderately pubescent; moderately glossy. Color: Close to 146B with random spots, close to 144B to 144C.

*Reproductive organs*.—Androecium (present only on disc florets): Quantity per floret: Five. Filament length: About 3 mm. Filament color: Close to 153D. Anther length: About 3 mm. Anther width: About 0.5 mm. Anther shape: Narrowly oblong. Anther color: Close to 203C. Pollen amount: Moderate. Pollen color: Close to 23A. Gynoecium (present only on disc florets): Quantity per floret: One. Pistil length: About 6 mm. Style length: About 5 mm. Style color: Close to 151B. Stigma diameter: About 3.5 mm. Stigma shape: Decurrent, cleft. Stigma color: Close to 200A. Ovary color: Close to 145D. Seeds and fruits: Seed and fruit development have not been observed on plants of the new *Echinacea* to date.

Disease & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be suitable for USDA Hardiness Zones 3 to 10.

It is claimed:

1. A new and distinct *Echinacea* plant named 'Sweet342' as illustrated and described.

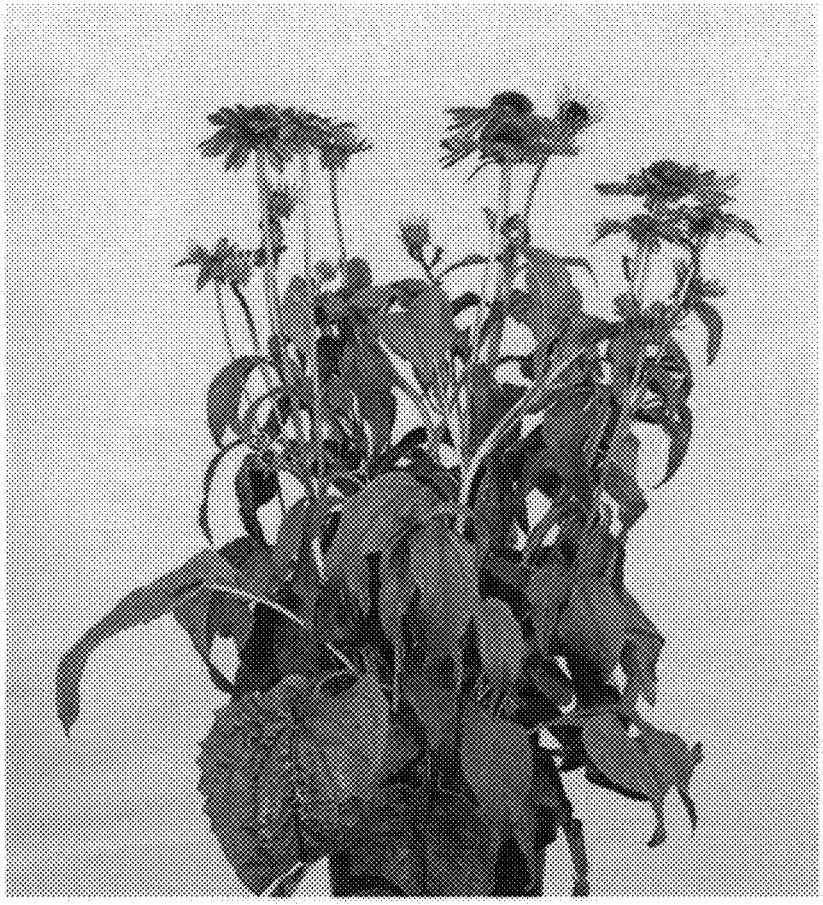
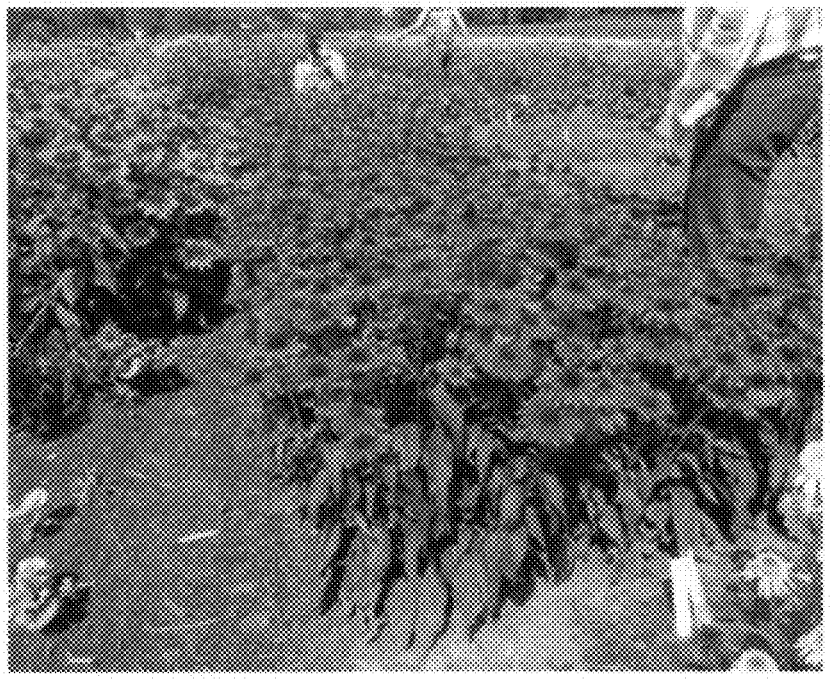

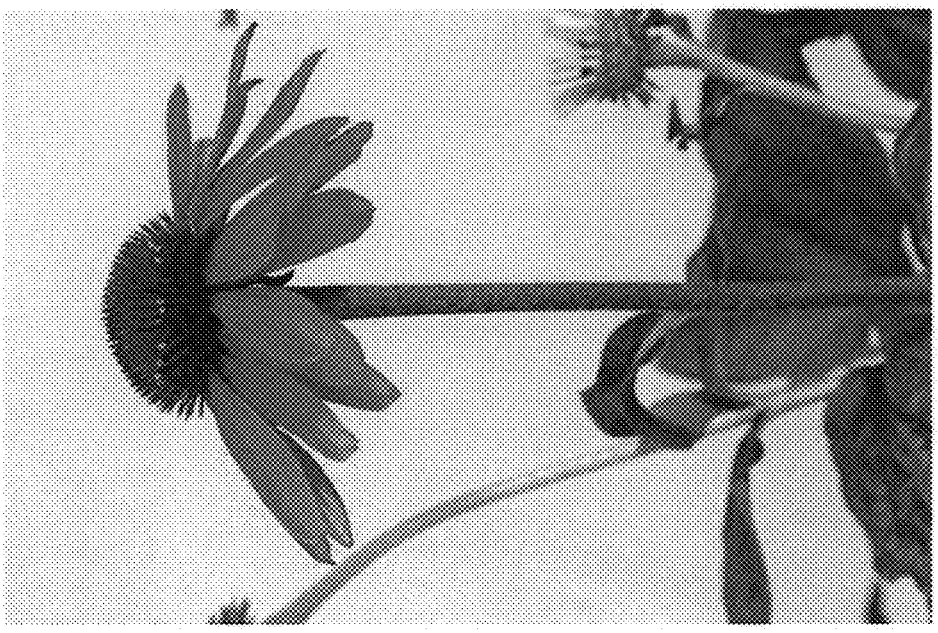
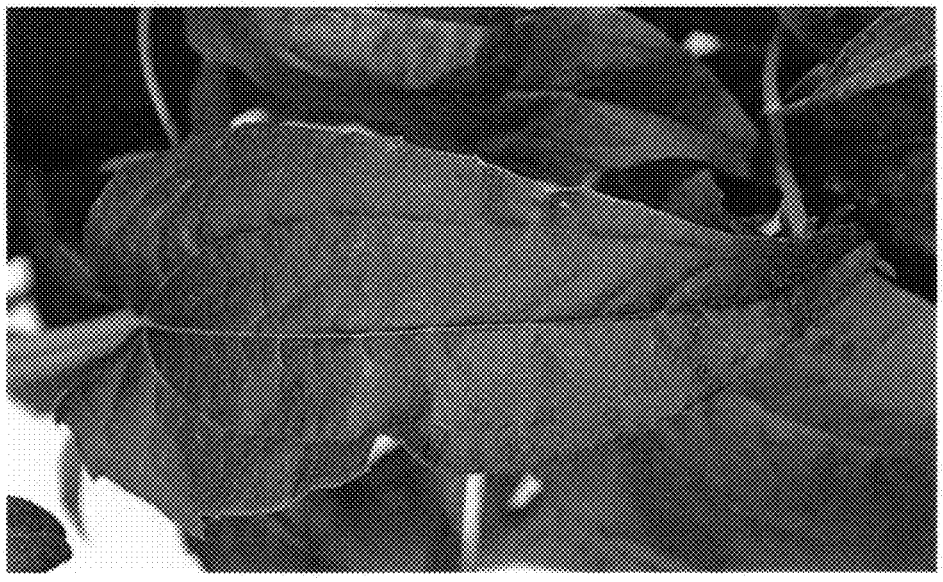

* * * * *